United States Patent [19]

Imai et al.

[11] Patent Number: 4,665,271

[45] Date of Patent: May 12, 1987

[54] NOVEL MOTOR FUEL ALKYLATION CATALYST AND PROCESS FOR THE USE THEREOF

[75] Inventors: Tamotsu Imai, Mount Prospect; Joseph A. Kocal, Gurnee, both of Ill.

[73] Assignee: UOP Inc., Des Plaines, Ill.

[21] Appl. No.: 887,778

[22] Filed: Jul. 21, 1986

Related U.S. Application Data

[62] Division of Ser. No. 764,707, Aug. 12, 1985.

[51] Int. Cl.$^4$ .............................................. C07C 3/54
[52] U.S. Cl. ................................................... 585/724
[58] Field of Search ......................................... 585/724

[56] References Cited

U.S. PATENT DOCUMENTS

| | | | |
|---|---|---|---|
| 3,531,546 | 9/1970 | Hervert | 585/724 |
| 3,761,540 | 9/1973 | Hutson et al. | 585/723 |
| 3,778,489 | 12/1973 | Parker et al. | 585/724 |

Primary Examiner—Curtis R. Davis
Attorney, Agent, or Firm—Thomas K. McBride; John F. Spears, Jr.

[57] ABSTRACT

A novel hydrocarbon alkylation catalyst is disclosed comprising a mineral acid and an ether component. A process for utilizing the novel catalyst is also disclosed.

2 Claims, No Drawings

NOVEL MOTOR FUEL ALKYLATION CATALYST AND PROCESS FOR THE USE THEREOF

CROSS REFERENCE TO RELATED APPLICATIONS

This is a Division of co-pending application Ser. No. 764,707 filed Aug. 12, 1985.

BACKGROUND OF THE INVENTION

This invention relates to a novel catalyst for the alkylation of an isoparaffin with an olefin acting agent. Additionally, the invention relates to a process in which the novel catalyst is used to produce an alkylate having improved antiknock properties. Accordingly, the invention has particular utility in the production of high octane alkylate for use as a motor fuel blending component.

Alkylation of isoparaffinic hydrocarbons, such as isobutane and isopentane, with olefinic hydrocarbons such as propylene, butylene and amylenes or with other olefin-acting agents such as $C_3$–$C_5$ alkyl halides, etc., using mineral acids such as hydrogen fluoride is well known as a commercially important method for producing gasoline boiling range hydrocarbons. The $C_5$–$C_{10}$ hydrocarbons typically produced in isoparaffin-olefin alkylation operations are termed "alkylate." Alkylate is particularly useful as a motor fuel blending stock. It possesses motor and research octane ratings high enough that it may be employed to improve overall octane ratings of available gasoline pools to provide motor fuels which comply with the requirements of modern automobile motors. High octane alkylate blending components are particularly important in producing motor fuels of sufficiently high octane when it is desired to avoid use of alkyl lead antiknock compounds in gasoline. A continuing goal in the art is to provide an economically attractive acid catalyzed alkylation process which provides an alkylate product having motor and research octane ratings which are higher than are attainable in conventional alkylation processes. This goal takes on special significance with the phaseout of alkyl lead antiknock compounds as blending agents for gasoline as mandated by government regulation.

In commercial isoparaffin-olefin alkylation operations using acid catalysts, generally, isobutane is the isoparaffin used and propylene, butylene and amylenes or a mixture of these olefins, are used as the olefin-acting agent. Typically the acid catalyst will comprise hydrogen fluoride. In conventional operations, the isoparaffin, olefin-acting agent and hydrogen fluoride catalyst are first contacted and thoroughly admixed in an alkylation reactor, forming a reaction mixture, or emulsion. After a relatively short time, the alkylation reaction is substantially complete and the reaction mixture is withdrawn from the alkylation reactor and is allowed to settle by gravity into immiscible hydrocarbon and catalyst phases in a settling vessel. The hydrogen fluoride catalyst phase thus separated is returned to the alkylation reactor for further catalytic use. The hydrocarbon phase separated in the settling operation is further processed, e.g., by fractionation, to recover an alkylate product and to separate unconsumed isoparaffin for recycle to the alkylation reactor. The recovered alkylate product may then be added to the motor fuel octane pool as a blending component. It is, therefore, desirable that the alkylate product have as high a research octane number as possible.

OBJECTS AND EMBODIMENTS

It is, therefore, an object of the present invention to provide an improved catalyst for the alkylation of an isoparaffin with an olefin acting agent. An alternative object is to employ the improved catalyst in an alkylation process to produce an alkylate having superior antiknock properties.

Accordingly, in one embodiment the present invention is a catalyst for the alkylation of an isoparaffin with an olefin acting agent comprising an anhydrous, nonalcoholic mixture of from about 50 to about 99 wt. % mineral acid and from about 1 to about 50 wt. % ether component.

In an alternative embodiment the present invention is a process for the alkylation of an isoparaffin with an olefin acting agent comprising mixing the isoparaffin and olefin acting agent at alkylation conditions in the presence of a catalyst comprising an anhydrous, nonalcoholic mixture of from about 50 to 99 wt. % mineral acid and from about 1 to about 50 wt. % ether component.

These as well as other objects and embodiments will become apparent upon review of the following more detailed description of the prior art and the invention.

INFORMATION DISCLOSURE

The art has recognized the use of acid catalyst modifiers in the process of alkylating an isoparaffin with an olefin. For example, U.S. Pat. No. 3,761,540 discloses that an isoparaffin may be alkylated with an olefin using hydrogen fluoride catalyst and a small proportion of $BF_3$. The $BF_3$ is disclosed as modifying the alkylation reaction in such a fashion as to minimize production of ethyl fluoride. The reference discloses that when the isoparaffin to olefin ratio in the reaction zone is less than about 4:1 a high octane value alkylate may be made by modifying the HF catalyst with $BF_3$ while minimizing alkyl fluoride formation.

U.S. Pat. No. 3,531,546 discloses the alkylation of organic compounds in the presence of a novel catalyst comprising a hydrogen fluoride-carbon dioxide complex. It is disclosed that by using the hydrogen fluoride-carbon dioxide complex a motor fuel alkylate having increased research octane number is thereby produced. The increased octane number results from improved isomer distribution in the alkylate.

A particular interest is U.S. Pat. No. 3,778,489. This reference discloses an alkylation process for alkylating alkanes with an alkene utilizing various strong acids including hydrofluoric acid in the presence of a catalyst promoter. At column 3, line 61 of the reference, it is disclosed that the preferred catalyst promoters contain either a hydroxy group such as alcohols or a hydroxy group precursor such as ethers which cleave to form alcohols under the acidic conditions of the subject invention. The most preferred compounds are disclosed to be the lower molecular weight alcohols such as ethyl alcohol, the lower molecular weight ethers such as diethyl ether and water. Accordingly, this reference discloses that ether compounds may be employed in the alkylation of alkanes and alkenes under conditions which promote the cleavage of the ethers to form alcohol. These ethers, therefore, do not act as catalyst in that they are not inert but rather cleave to form different compounds and are thereby consumed in the alkylation reaction. By way of distinction the present invention employs ether compounds as actual catalysts, the conditions within the alkylation process being such to preserve the ether and inhibit any cleavage thereof to an alcohol.

In summary then the art has disclosed the use of catalyst promoters and in particular has disclosed the use of ether as a precursor of an alcoholic promoter. However, the art has not disclosed a catalyst comprising a strong acid such as hydrofluoric acid and an ether compound in which catalyst the ether is maintained as an ether as opposed to being cleaved to an alcohol. Rather in the instant invention the ether acts as a true catalyst component being substantially unconsumed in the alkylation process.

DETAILED DESCRIPTION OF THE INVENTION

To reiterate briefly the present invention relates to a catalyst for the alkylation of an isoparaffin with an olefin acting agent comprising an anhydrous, nonalcoholic mixture of from about 50 to about 99 wt. % mineral acid and from about 1 to about 50 wt. % ether component. Additionally, the invention relates to an alkylation process utilizing this novel catalyst.

As heretofore indicated the catalyst of the instant invention is for the alkylation of an isoparaffin with an olefin acting agent. Typical of the isoparaffins which may be utilized in the invention are isobutane, isopentane and similar isoparaffins. The preferred isoparaffins are isobutane and isopentane, particularly, isobutane. A mixture of two or more isoparaffins may also be employed, if desired. Conventional isobutane alkylation feedstocks are suitable for use in the present process. Such conventional isobutane feedstocks may contain some nonreactive hydrocarbons such as normal paraffins. For example, a conventional commercial isobutane alkylation feedstock generally contains about 95 wt. % isobutane, 4 wt. % normal butane and 1 wt. % propane.

Olefin-acting agents which are suitable for use in the process of the present invention include $C_3$–$C_6$ monoolefins, alkyl halides, or mixtures thereof. $C_3$–$C_5$ olefins are preferred. The process of the present invention may be applied to the alkylation of mixtures of two or more olefin acting agents with the same benefits and improvements as would be obtained in using a single olefin-acting agent. For example, many conventional olefin feedstocks utilized in commercial alkylation operation contain mixtures of propylene and butylenes, or propylene, butylenes and amylenes. Application of the present process to such olefin mixtures results in improvements in quality of the products obtained which are equal to the improved obtained using a single olefin. Similarly, a mixture of $C_3$–$C_5$ alkyl halides and olefins in any proportion is also suitable in many cases, for example, when the halide is fluoride. The particularly preferred $C_3$–$C_5$ olefin feedstocks are conventionally derived from petroleum refining processes such as catalytic cracking and may contain substantial amounts of saturates, lighter and heavier olefins, etc. Olefin feedstocks derived from such conventional sources are suitable for use in providing the olefin-acting compound used in the present process.

As heretofore indicated the catalyst of the present invention comprises an anhydrous, nonalcoholic mixture of mineral acid and ether component. It should be understood that by the term anhydrous it is meant that the water content of the acid should comprise no more than about 3 wt. % based on the total weight of the acid phase. The presence of water in the acid phase greatly increases the corrosive properties of the mineral acid, especially hydrofluoric acid, and results in the cleavage of the ether component to an alcohol. As will be more fully appreciated upon review of the appended examples substitution of an alcohol component for the ether component of the present invention yields inferior results. In this last respect it is a feature of the present invention that the catalyst be nonalcoholic. By nonalcoholic it is meant that the alcohol content of the acid phase be no more than about 3 wt. % based on the weight of the acid phase.

Mineral acids which may be employed in the present invention comprise any mineral acid commonly used in alkylation processes. Such acids include sulfuric acid, halosulfuric acids such as fluorosulfuric acid or halogen acids such as hydrofluoric acid, etc. It is to be further understood that the term mineral acid is intended to encompass solid acid sources such as acidic resins or zeolites which are suitable for catalyzing the alkylation of an isoparaffin with an olefin acting agent. Especially preferred is the use of hydrofluoric acid.

Hydrofluoric acid is preferred because it is one of the most stable mineral acids. It can be subjected to high temperatures and pressures and to the action of other catalytic agents without being broken down. Many of its organic compounds decompose either by heat alone or in the presence of catalyst to regenerated hydrofluoric acid. This results in low catalyst consumption in the process. An important advantage of using hydrofluoric acid is that, by virtue of its chemical stability and low freezing point, it may be employed over a wide range of operating conditions. Conditions may be employed which are most satisfactory thermodynamically or economically, without limitations due to catalyst properties. For example, in the alkylation reaction, ambient or slightly superambient temperatures may be used with hydrofluoric acid. Hence, it is unnecessary to utilize refrigeration as might be the case when certain other mineral acids are utilized as the alkylation caalysts. The vapor pressure of hydrofluoric acid makes it unnecessary to resort to extreme pressures to maintain the catalyst in liquid phase. It freezing point permits its use at temperatures much lower than is possible with most catalyst which either freeze or become highly viscous at low temperatures. Although in the alkylation of isobutane with olefins to produce aviation blending fuel, the usual operating conditions are of the order of about 30° C., there are catalytic reactions which are favored by low temperaturs. Since hydrofluoric acid catalyzes such reactions, it is a distinct advantage because of its physical properties. Conversely since hydrofluoric acid is thermally stable it can be employed at much higher temperatures than other alkylation catalysts. This is a unique property of hydrofluoric acid.

As heretofore indicated the catalyst of the present invention comprises from about 70 to about 95 wt. % mineral acid based on the weight of the acid catalyst. It is especially preferred that the invention comprise between about 85 and 95 wt. % mineral acid. This is especially true when the acid comprises hydrofluoric acid. A particularly preferred catalyst composition comprises about 90 wt. % hydrofluoric acid based on the weight of the acid phase.

A second feature of the present invention is an ether component. As heretofore indicated the art has been cognizant of utilizing ether as an additive for alkylation processes; however, in the prior art the ether was taught to be an alcohol precursor. Accordingly, the art is directed towards an alkylation process wherein an alcohol or alcohol precursors comprise a catalyst modifier. In contradistinction the present invention is directed toward a catalyst wherein the ether component is a true catalyst component in that the ether is not consumed in the reaction.

Any suitable ether may be utilized as the ether component. For example, the ether component may comprise lower molecular weight ether such as dimethyl ether, diethyl ether, dipropyl ether, etc. It is preferred, however, that the other component comprise an ether that will be liquid at the conditions employed within the alkylation reaction zone. A particularly preferred ether component comprises methyl tert-butyl ether. Of course, it should be understood that the ether component may comprise a single ether species such as the preferred methyl tert-butyl ether, or the either component may comprise a mixture of two or more ethers.

Alkylation conditions which may be employed in the process of the present invention include a temperature of from about 0° F. to about 200° F., a pressure sufficient to maintain the reactants and the catalyst in the liquid phase, and a contact time between the hydrocarbons and the catalyst of about 0.1 minute to about 30 minutes. In a preferred embodiment utilizing a catalyst comprising hydrogen fluoride and methyl tert-butyl ether, a catalyst/hydrocarbon volume ratio of about 1:1 to about 5:1 is preferred, and a temperature of about 50° F. to about 150° F. is preferably employed in the alkylation reaction zone.

In a particularly preferred embodiment, a reaction mixture of a catalyst comprising hydrogen fluoride and methyl tert-butyl ether, reactants and reaction products formed in the alkylation reactor is passed through a reaction soaker. In the description of the preferred embodiments herein provided it is intended that both the alkylation reactor and a reaction soaker, if one is utilized, are included within the scope of the term "alkylation reaction zone." Suitable reaction soakers are well known in the art. For example, the reaction soakers described in U.S. Pat. Nos. 3,560,587 and 3,607,970 may suitably be employed in the present process. Such reaction soakers are conventionally vessels equipped with perforated trays, baffle sections, or the like to maintain an alkylation reaction mixture in the form of a fairly homogeneous mixture, or emulsion, for a predetermined length of time. The alkylation reaction mixture of catalyst and hydrocarbons is maintained in the reaction soaker for a time which depends on the composition of the reaction mixture. Generally a reaction soaker residence time of about 1 minute to about 30 minutes is employed. The temperature and pressure maintained in the reaction soaker are substantially the same as the temperature and pressure maintained in the associated alkylation reactor.

Means for settling the reaction mixture effluent from the alkylation reaction zone in order to separate a settled hydrocarbon phase and an acid catalyst phase as well known in the alkylation art. Generally, the effluent alkylation reaction mixture recovered from an alkylation reaction or soaker comprises a mixture of unreacted isoparaffins, alkylation reaction products, acid catalyst, and catalyst-soluble organic materials, possibly with small amounts of light hydrocarbons, etc. When this alkylation reaction mixture is allowed to stand unstirred, i.e., settled, the alkylation reaction products, isoparaffins and light hydrocarbons form a lighter settled hydrocarbon phase. The acid catalyst phase comprising a mineral acid and ether component forms a separate phase. The settled hydrocarbon phase is then simply mechanically separated from the catalyst phase. The temperature and pressure maintained during such a settling operation are substantially the same as those described above in connection with the alkylation conditions employed in the reaction zone. The hydrocarbons and the catalyst are preferably in the liquid phase during the settling separation operation.

Some means for withdrawing heat from the alkylation zone may be necessary for optimum operation of the process. A variety of means for accomplishing the heat withdrawal are well known. For example, the heat generated in the alkylation reaction may be withdrawn from the alkylation reactor by indirect heat exchange between cooling water and the reaction mixture in the reactor.

In order to demonstrate the benefits and advantages of the present invention in contrast to prior art alkylation methods the following examples are offered. It is to be understood that the examples are intended to be illustrative and in no way restrictive on the otherwise broad embodiments of the present invention as set forth in the claims appended hereto.

EXAMPLE I

This example was conducted in a pilot plant scale unit operation. The pilot plant comprises a monel autoclave in which the isoparaffin and olefin-acting agent are contacted with the acid catalyst. After sufficient time the hydrocarbon and acid phases were removed from the autoclave and passed to a settler in which the phases were allowed to separate. The acid phase was then removed from the settler and recycled back to the autoclave for contact with more hydrocarbon. The hydrocarbon phase comprising alkylate was removed from the settler and passed to neutralization facilities. Thereafter the hydrocabon phase was collected for analysis.

In this example two different runs were made in the pilot plant. The first run employed an acid catalyst comprising 90 wt. % hydrogen fluoride and 10 wt. % organic diluent. The organic diluent comprises oligomerized isobutylene of $C_7$ to $C_{23}^+$ carbon number range with mostly $C_8$ to $C_{12}$ hydrocarbon. The second run employed a catalyst comprising 90 wt. % hydrogen fluoride and 10 wt. % methyl tert-butyl ether. In both tests the conditions within the autoclave were a temperature of 20° C., a pressure of 130 psig, a residence time of 10 minutes, and a stirring rate of 1800 rpm. The volume ratio of acid phase to hydrocarbon phase in the autoclave was 1.5. The mole ratio of isobutane to $C_4$ olefins was 7.9. The $C_4$ olefin distribution was 48.2% 2-butene, 23.2% 1-butene, and 28.6% isobutylene.

In each run the alkylate product was analyzed and the products were found to have the following compositions and research octane numbers.

| Catalyst | HF/Organic Diluent | HF/Methyl Tert-Butyl Ether |
|---|---|---|
| Alkylate Composition: | | |
| $C_8^-$ | 8.3 wt. % | 6.4 wt. % |
| Trimethyl Pentane | 72.6 wt. % | 75.7 wt. % |
| Dimethyl Hexane | 13.9 wt. % | 12.0 wt. % |
| $C_8^+$ | 5.2 wt. % | 5.9 wt. % |

-continued

| Catalyst | HF/Organic Diluent | HF/Methyl Tert-Butyl Ether |
|---|---|---|
| Research Octane No.: | 95.5 | 96.4 |

As can be readily seen when the acid catalyst comprised an ether component the research octane number was 0.9 higher than an acid catalyst comprising hydrogen fluoride and an organic diluent. The higher octane achieved by means of the invention is a direct result of forming more trimethyl pentanes than dimethyl hexanes in the alkylate. The increase in the trimethyl pentane content of the alkylate and decrease in the dimethyl hexane content is a result of the presence of the ether compound.

EXAMPLE II

In this example two further alkylation experiments were conducted to determine the stability of the ether component of the acid catalyst. Two actual alkylation runs were conducted in the pilot plant described in Example I above. The conditions employed in both alkylation experiments were substantially the same as those employed in the test conducted in Example I. In this example one experiment was conducted for 24 hours with hydrocarbon feed being cut into the plant for only about 5 hours while the second experiment in the pilot plant was conducted for 16 days with hydrocarbon being cut into the plant for only 54 hours. However, the acid catalysts were maintained in the plant for 24 hours and 16 days, respectively. At the end of each run the acid phase was analyzed. The results of the analyses are set forth in the table below.

| Duration of Test: | 1 Day | 16 Days |
|---|---|---|
| Acid Phase Analysis: | | |
| HF | 90.3 wt. % | 90.2 wt. % |
| Methyl Tert-Butyl Ether | 9.0 wt. % | 8.2 wt. % |
| Methanol | 0.1 wt. % | 0.7 wt. % |
| H$_2$O | 0.5 wt. % | 0.6 wt. % |
| Unknown | 0.1 wt. % | 0.3 wt. % |

As can be seen from the data above only a small amount of the methyl tert-butyl ether decomposed to methanol. It is believed that the amount of methyl tert-butyl ether which did dissociate to methanol did so because of the presence of water as a contaminant. Irrespective of this, it is to be noted that the vast majority of the methyl tert-butyl ether remained unconverted to methanol.

EXAMPLE III

In this example a further run was conducted in the alkylation pilot plant. The conditions employed during this run were substantially the same as those set forth in the previous two examples. However, in this case the acid catalyst comprised 90 wt. % hydrogen fluoride and 10 wt. % methanol.

The results of the test are set forth in the table below. In addition to the results of the test from this Example there is also included in the Table the results from Example I where the catalyst comprised hydrogen fluoride and methyl tert-butyl ether.

| Catalyst | HF/METHANOL | HF/Methyl Tert-Butyl Ether |
|---|---|---|
| Alkylate Composition: | | |
| C$_8$⁻ | 9.8 wt. % | 6.4 wt. % |
| Trimethyl Pentane | 72.9 wt. % | 75.7 wt. % |
| Dimethyl Hexane | 11.7 wt. % | 12.0 wt. % |
| C$_8$⁺ | 5.6 wt. % | 5.9 wt. % |
| Research Octane No. | 96.0 | 96.4 |

As can be readily seen by comparison of the data in the table above, use of an acid catalyst comprising an ether component gives superior results to use of an acid catalyst comprising an alcohol component. Use of the ether component resulted in an octane increase of 0.4 Research Octane numbers over use of the acid catalyst comprising methanol. This increase in octane can be attributed to the increased amount of trimethylpentane produced (75.7 wt. % versus 72.9 wt. %) and a concomitant reduction in dimethyl hexanes.

In summary then it can be seen that by use of an alkylation catalyst comprising an ether component there can be achieved an alkylate of increased octane number and more desirable isomer distribution.

What is claimed is:

1. A process for the alkylation of an isoparaffin with an olefin acting agent comprising mixing the isoparaffin and olefin acting agent at alkylation conditions in the presence of a catalyst comprising an hydrous, nonalcoholic mixture of from about 50 to 99 wt. % hydrofluoric acid and from about 1 to about 50 wt. % methyl tert-butyl ether.

2. The process of claim 1 further characterized in that the isoparaffin comprises isobutane and the olefin acting agent comprises C$_4$ olefins.

* * * * *

UNITED STATES PATENT AND TRADEMARK OFFICE
CERTIFICATE OF CORRECTION

PATENT NO. : 4,665,271
DATED : May 12, 1987
INVENTOR(S) : Imai et al.

It is certified that error appears in the above-identified patent and that said Letters Patent is hereby corrected as shown below:

In Column 8, line 44: Change "hydrous" to --anhydrous--.

Signed and Sealed this

Eleventh Day of August, 1987

Attest:

DONALD J. QUIGG

Attesting Officer

Commissioner of Patents and Trademarks